United States Patent
Prakash et al.

(10) Patent No.: US 6,825,384 B1
(45) Date of Patent: Nov. 30, 2004

(54) BROMINE FREE TEMPO BASED CATALYST SYSTEM FOR OXIDATION OF PRIMARY AND SECONDARY ALCOHOLS USING NAOCL AS AN OXIDANT

(75) Inventors: Indra Prakash, Hoffman Estates, IL (US); Setrak K. Tanielyan, Maplewood, NJ (US); Robert L. Augustine, Livingston, NJ (US); Kenneth E. Furlong, Evans, GA (US); Robert C. Scherm, Evans, GA (US); Handley E. Jackson, North Augusta, SC (US)

(73) Assignee: The NutraSweet Company, Chicago, IL (US)

( * ) Notice: Subject to any disclaimer, the term of this patent is extended or adjusted under 35 U.S.C. 154(b) by 0 days.

(21) Appl. No.: 10/767,805

(22) Filed: Jan. 29, 2004

(51) Int. Cl.[7] .......................... C07C 45/29; C07C 45/30
(52) U.S. Cl. ...................... 568/402; 568/407; 568/471; 568/472
(58) Field of Search ................. 568/402, 407, 568/471, 472

(56) References Cited

U.S. PATENT DOCUMENTS

| | | | | |
|---|---|---|---|---|
| 5,770,775 A | * | 6/1998 | Katritzky et al. | 6/199.8 |
| 5,821,374 A | * | 10/1998 | Jenny et al. | 549/263 |
| 5,856,584 A | * | 1/1999 | Prakash et al. | 568/449 |
| 5,973,209 A | * | 10/1999 | Prakash et al. | 10/199.9 |
| 6,127,573 A | * | 10/2000 | Li et al. | 562/419 |
| 6,335,464 B1 | * | 1/2002 | Ochi et al. | 562/512.2 |
| 6,451,943 B1 | * | 9/2002 | Burkhardt et al. | 526/265 |
| 6,518,419 B1 | * | 2/2003 | Van Der Lugt et al. | 536/105 |
| 6,573,409 B1 | * | 6/2003 | Ebner et al. | 568/449 |

OTHER PUBLICATIONS

Ma et al. Organic Oxoammonium Salts. A New Convenient Method for the Oxidation of Alcohols to Aldehydes and Ketones. Journal of Organic Chemisty. 1991, vol. 56, p. 6110–6114.*

* cited by examiner

*Primary Examiner*—Samuel Barts
*Assistant Examiner*—Sikarl A. Witherspoon
(74) *Attorney, Agent, or Firm*—Jeffrey M Hoster

(57) ABSTRACT

The present invention relates to a process of oxidation of alcohols selectively to aldehydes or ketones with NaOCl using a TEMPO—borate catalyst system. It is shown that the oxidation can be efficiently carried out without KBr additives under solvent free conditions. Aldehydes such as 3,3-dimethylbutyraldehyde can be produced efficiently using the present invention.

32 Claims, No Drawings

US 6,825,384 B1

BROMINE FREE TEMPO BASED CATALYST SYSTEM FOR OXIDATION OF PRIMARY AND SECONDARY ALCOHOLS USING NAOCL AS AN OXIDANT

FIELD OF THE INVENTION

The present invention relates to bromine free catalyst system, which exhibits high activity and selectivity in the oxidation of alcohols to aldehydes or acids using NaOCl as an oxidant. More specifically, the invention relates to a catalyst system, which comprises a synergistic couple of 2,2,6,6,-tetramethylpiperidinyloxy catalyst (hereinafter referred to as "TEMPO" or "TEMPO catalyst") and $Na_2B_4O_7$ co-catalyst (CC), which is more active and shows higher selectivity than the known TEMPO—NaBr system. Such a synergistic couple is particularly useful for, but not limited to, oxidation of primary aliphatic and aromatic alcohols. The system also permits carrying out the oxidation without the need for solvents.

BACKGROUND OF THE INVENTION

The catalytic oxidation of alcohols selectively to carbonyl compounds is probably one of the most important transformations in the synthetic organic chemistry. A large number of oxidants have been reported in the literature and most of them are based on transition metal oxides such as chromium and manganese (S. Kirk-Othmer Mitchell, Enciclopedia of Chemical Technology, $4^{th}$ ed., Wiley-Interscienc, New York, Vol.2, p 481, (1992); Hudlicky, M. "Oxidations in Organic Chemistry", ACS Monograph No.186 American Chemical Society Washington D.C. (1990); Sheldon R. A., Kochi J. K. Metal Catalized Oxidation of Organic Compounds. New York, Academic Press, 1981; Ley, S. V., Madin, A,. In comprehensive Organic Synthesis, Trost B., Fleming, I., Eds.; Pergamon Oxford, 1991; Vol 7, p251; Mijs. W. J., DeJonge, C.R.H.I. Organic Synthesis by Oxidation with Metal Compounds ; Plenum: New York, 1968). Since most of the oxidants and the products of their transformation are toxic species, their use creates serious problems concerning their handling and disposal. A serious drawback to the use of these reagents, for both cost and toxicity reasons, is the need to use them in large excess over the required reaction stoicheometry. The search for efficient, easily accessible catalysts and "clean" oxidants such as hydrogen peroxide, hydroperoxides or molecular oxygen for industrial applications is still a challenge (Dijksman, A., Arends I.W.C.E. and Sheldon R., Chem. Commun., 1999, 1591–1592; Marko I. E., P. R. Giles, Tsukazaki M., Brown S. M. and Urch C. J., Science, 19696, 274, 2044). A large number of transition metal complexes and oxidants have been reported to catalyze the selective oxidation of primary alcohols to aldehydes with varying levels of effectiveness such as $RuCl_3$-$NaBrO_3$ (Konemoto S., Tomoioka S., Oshima K.), Bull. Chem. Soc. Japan. 1986. V.59. N1, P.105), $Bu_4NRuO_4$-4-Methylmorpholine N-oxide (Griffith W. P., Ley S. V., Whitcombe G. P., White A. D)., Chem. Commun. 1987, N21, p.1625), $H_2O_2$ and tert-Butylhydroperoxide (t-BuOOH) (Y. Tsuji, T. Ohta, T. Ido et al.), J. Organometalic Chemistry, 270, 333 (1984), (T. M. Jiang, J. C. Hwang, H. O. Ho, C. Y. Chen). J. Chin. Chem. Soc., 35, 135, (1988). The methods described have only limited use since the overall yields are low and some of them require the application of precious metal complexes or expensive primary oxidants.

A particularly convenient procedure for the oxidation of primary and secondary alcohols is reported by Anelli and co-workers (J. Organic Chemistry, 1987, 52, 2559; J. Organic Chemistry, 1989, 54, 2970). The oxidation has been carried out in a two-phase system ($CH_2Cl_2$-water) utilizing the TEMPO as a catalyst and cheap and readily accessible NaOCl as an oxidant. The co-catalyst KBr enhances the reaction rate and the aqueous phase is buffered at pH 8.5–9.5 using $NaHCO_3$. The use of a quaternary ammonium salt as a phase transfer catalyst furthers the oxidation of alcohols to carboxylic acids. The same procedure was modified by using $NaClO_2$ as the oxidant in the presence of catalytic amounts of TEMPO and NaOCl. This led to the formation of the carboxylic acid as the main product (U.S. Pat. No. 6,127, 573).

Prakash et al. in U.S. Pat. No. 5,856,584 report a similar procedure for oxidation of 3,3-Dimethyl-1-butanol. According to this procedure the 3,3-Dimethyl-1-butanol is oxidized to 3,3-Dimethylbutyraldehyde with NaOCl in a two-phase system using $CH_2Cl_2$ as a reaction solvent. The stable 2,2,6,6-tetramethyl-1-piperidinyloxy free radical and KBr are used as an efficient catalytic system to produce the desired aldehyde in 80% isolated yield.

In another development of the TEMPO mediated oxidation of primary alcohols to aldehydes, Sheldon and co-workers have used a polymeric version of the TEMPO catalyst PIPO, obtained by oxidation of the commercially available poly[(6-[1,1,3,3-tetramethylbutyl)amino]-s-triazine-2,4-diyl][(2,2,6,6-tetramethyl-4-piperidyl)imino] hexamethylene[(2,2,6,6-tetramethyl-4-piperidinyl)imino]), known also as Chimasorb 944, (in Chem.Commun., 2000, 271–272). The procedure produces aldehydes in high yields in solvent free conditions only for aromatic alcohols. The oxidation of primary alcohols leads to significant over-oxidation to carboxylic acid.

U.S. Pat. No. 5,821,374 describes the use of N-chloro compounds such as N-chloro-4-toluenesulfonamide sodium salt (Chloramine T) or N-chloro-benzene sulfonamide sodium salt (Chloramine B) as an oxidant in the TEMPO catalyzed oxidation of primary alcohols to aldehydes. The major drawback to this method is the use of large amounts of solvents and the toxicity of the N-chlorinated aromatics used as oxidants.

U.S. Pat. No. 6,335,464 describes a polymer supported TEMPO catalyst which, combined with a NaBr co-catalyst, was used to electrocatalytically oxidize primary alcohols to carboxylic acids using NaOCl as the oxidant. There is no report on the use of the procedure for selectively forming the corresponding aldehydes and the possibility for re-use of the catalyst.

Despite the extensive work reported in the area of the selective oxidation of primary alcohols there is still a continuous need for developing highly efficient and economical oxidation methods which do not require the use of organic solvents, can be carried out with environmentally friendly oxidants and do not require the use of bromine based co-catalysts. It is the object of the present invention to provide such an oxidation method.

SUMMARY OF THE INVENTION

The process according to this invention comprises oxidizing primary or secondary alcohols with an oxidant in the presence of a catalyst of formula II or III and a co-catalyst.

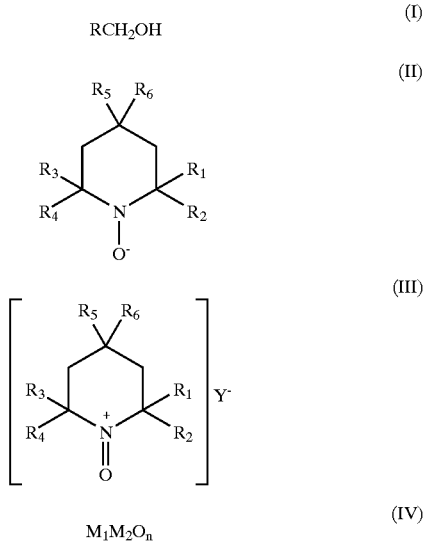

(I) RCH$_2$OH (II) [structure with R$_5$, R$_6$, R$_3$, R$_1$, R$_4$, R$_2$, N-O·]

(III) [structure with R$_5$, R$_6$, R$_3$, R$_1$, R$_4$, R$_2$, N$^+$=O] Y$^-$ (IV) M$_1$M$_2$O$_n$ In Formulas (II) and (III), $R_1$, $R_2$, $R_3$ and R4 independently are lower alkyl or substituted alkyl groups of the same or different structures. $R_5$ and R4 are hydrogen, alkyl or lower alkoxy or one is hydrogen and the other is lower alkoxy, hydroxy, amino, alkyl or dialkylamino, alkylcarbonyloxy, alkylcarbonylamino, or $R_5$ and $R_6$ are ketal. The Y$^-$ group is an anion.

The co-catalyst according to the invention is a polyoxy anion or metal salt having formula IV, where $M_1$ is a metal ion from Group IA or IIA and $M_2$ is an ion from Group IIIa, IVa, IVB, Va, VB, VIA, VIB, VIIB or VIII of the Periodic Table of Elements.

The TEMPO/co-catalyst promoted oxidation is described by the following reaction shown in Scheme 1. According to this, the oxidation takes place via a cascade mechanism in which a number of oxidizing species exist in a dynamic equilibrium. Formally, the hypochlorite anion oxidizes the co-catalyst (CC) to its oxidized form (CCO*), which in turn transfers the chain over to TEMPO oxoammonium salt. The "oxidized" form of TEMPO converts the primary alcohol to aldehyde in the last redox cycle. The reaction takes place at the pH of the bleach solution in the range of 8.6–9.5 in which the hypochlorite anion is relatively stable and at the same time the rate within the ClO$^-$/Cl$^-$–CC/CCO* is high enough to sustain high overall rates of alcohol oxidation. To maintain the desired pH, a NaHCO$_3$ or K$_2$CO$_3$ could be effectively used. Since the desired aldehyde under the current oxidizing conditions can easily undergo further conversion to the corresponding acid derivative, the reaction temperature is kept at or below 0° C.

DETAILED DESCRIPTION OF THE INVENTION

The process according to the invention comprises oxidizing primary or secondary

Scheme 1

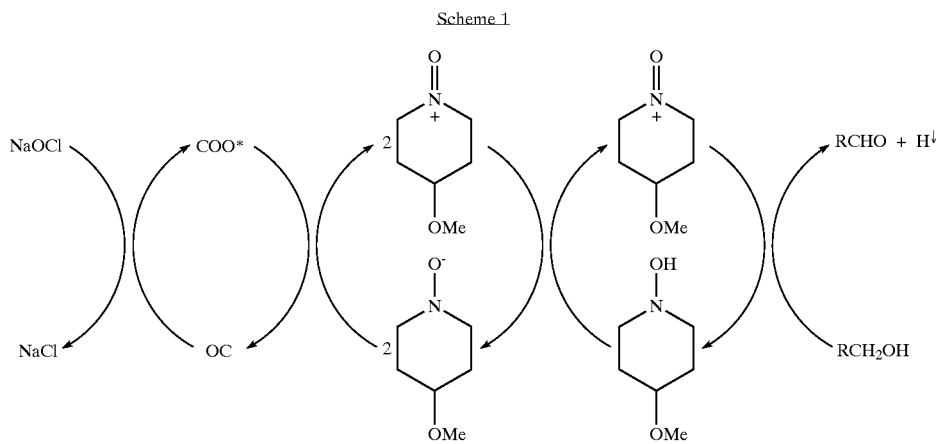

alcohols with an oxidant in the presence of a TEMPO based catalyst of formula II or III above and a co-catalyst of formula IV above.

The term primary or secondary alcohols as used in the present invention describes organic compounds having primary or secondary hydroxyl groups. The term lower alcohol as used herein refers to alcohols having 1 to 10 carbon atoms while the term higher alcohol as used herein refers to alcohols having 11 or more carbon atoms. Examples of primary and secondary alcohols thereof include alcohols such as methanol, ethanol, n- and isopropyl alcohol, n-, iso- and sec-butyl alcohol, pentyl alcohol, hexyl alcohol, neopentyl alcohol, neohexyl alcohol, octyl alcohol, lauryl alcohol, tridecyl alcohol, myristyl alcohol, nonadecyl alcohol, eicosyl alcohol. Examples of unsaturated alcohols include allyl alcohol, crotyl alcohol and propargyl alcohol. Examples of aromatic alcohols include benzyl alcohol, phenyl ethanol, phenyl propanol and the like. The term TEMPO based catalyst as used herein refers to compounds of formula II or III above. Here, $R_1$, $R_2$, $R_3$ and R4 independently are lower alkyl or substituted alkyl groups of the same or different structures. $R_5$ and $R_6$ are both hydrogens, alkyl or are lower alkoxy or one is hydrogen and the other is lower alkoxy, hydroxy, amino, alkyl or dialkylamino, alkylcarbonyloxy, alkylcarbonylamino, or can jointly be an oxygen or ketal. The $Y^-$ group is an anion. The $Y^-$ group is an anion. The term "lower alkyl" means straight chain or branched saturated hydrocarbon groups with up to 8 carbon atoms, such as methyl, ethyl, n-propyl, isopropyl, isobutyl, pentyl, n-hexyl and the like. The term "lower alkoxy" means lower alkyl groups bonded via an oxygen atom, such as methoxy, ethoxy and the like. The term "lower alkylcarbonyloxy means lower alkylcarbonyl group bonded via an oxygen atom. The term "lower alkylcarbonyl" means lower alkyl groups bonded via carbonyl group and is represented by groups such as acetyl, propionyl and the like. The term "lower carbonylamino" means lower alkylcarbonyl group bonded via nitrogen atom such as acetylamino and the like.

Examples of such compounds include, but are not limited to 2,2,6,6,-tetramethylpiperidine N-oxyl (TEMPO) and the 4-substituted derivatives thereof including 4-methoxy-TEMPO, 4-ethoxy-TEMPO, 4-acetoxy-TEMPO, 4-acetamino-TEMPO, 4-hydroxy-TEMPO, 4-benzoyloxy-TEMPO, 4-amino -TEMPO, N, N-dimethylamino-TEMPO, 4-oxo-TEMPO and the polymeric versions of TEMPO such as poly [(6-[1,1,3,3-tetramethylbutyl)amino]-s-triazine-2,4-diyl], [(2,2,6,6-tetramethyl-4-piperidyl)imino] hexamethylene[(2,2,6,6-tetramethyl-4-piperidinyl)imino]], known also as Chimasorb 944.

The co-catalyst according to the invention is selected from the group consisting of oxymetal ions or metal salts which contains at least one metal atom or ion from Group IIa, IIIa, IVa, Va, Via, VIIa or VIII of the Periodic Table of Elements. Suitable oxyrnetal cations that can be employed in the present invention include, but not limited to: $TiO^{2+}$, $VO^{2+}$, $CrO_2^{2+}$, $ZrO^{2+}$, $MoO_2^{2+}$, $WO_2^{2+}$. The anionic species used in forming the salts be chlorides, phosphates, sulfates, acetates, acetylacetonates and the like. Suitable oxymetal anions that can be employed in the present invention include but are not limited to: $MoO_4^{2-}$, $WO_4^{2-}$, $VO_3^-$, $H_2PO_4^{2-}$, $B_4O_7^{2-}$ and the like. The cationic species used in forming the salt may be ammonium, tetra alkylammonium, alkali metal, alkaline earth or other suitable cations. More particularly, it is preferable to use $Na_2B_4O_7$ or ZrO (acetate)$_2$.

The term oxidant as used herein means compounds capable of either transferring active oxygen to the co-catalyst or directly oxidizing the reduced form of the TEMPO catalyst (see Scheme 1). Suitable oxidizing agents that can be employed include, but are not limited to chlorite, chlorate, bromate, hypochlorite, hypobromite, hydrogen peroxide, organic hydroperoxides, percarboxylic acids and the like. More particularly, sodium hypochlorite, potassium hypochlorite, calcium hypochlorite, sodium hypobromite or potassium hypobromite are used. Commercial scale bleach is especially preferred. Bleach can be used as is or can be modified by any inorganic salt such as chloride, sulfate, carbonate of sodium, potassium, magnesium, bases such as sodium or potassium carbonates, bicarbonates, or acids such as acetic, hydrochloric, or sulfuric to improve the ionic strength and modify the pH.

The presence of solvents in the process of the invention is not critical. The reaction can be carried out in neat alcohol with the same efficiency and the same level of selectivity. In the instances when the alcohol to be oxidized is solid at the reaction temperatures employed, any conventional non-polar, aprotic solvent may be used. Particularly preferred solvents include but are not limited to methylene chloride, chloroform, ethyl acetate, butyl acetate, acetonitrile, tetrahydrofuran, toluene, acetone, diethyl ether, methyl tert-butyl ether, pentane, hexane or a mixture of such solvents. Especially preferred solvents are heptane, toluene and ethyl acetate.

Inorganic salt addition to the reaction system increases the ionic strength of the system and lowers the freezing point of the aqueous buffer solution. Such depression in the freezing point of the reaction mixture is needed when the oxidation reaction is carried out in solvent-free conditions. Suitable inorganic salts are selected from the group including, but not limited to, sodium chloride and potassium chloride.

The accumulation of small amounts of organic acid and HCl may drive the pH of the reaction solution to lower values and will cause reduction in the reaction rate. Therefore, to achieve maximum rate and high product selectivity, the oxidation reaction is preferably carried out in presence of an aqueous buffer or base to intercept the acidic by-products formed. Suitable buffering agents and base compounds are selected from the group including but not limited to $NaHCO_3$, $KHCO_3$, $Na_2CO_3$, $K_2CO_3$, $K_2PO_4$, $Na_2HPO_4$, $NaH_2PO_4$, $K_2HPO_4$, $KH_2PO_4$, NaOAc. They are used in amounts sufficient to maintain a pH of about 4–12 and most preferably 8.6–9.5.

The reaction can be carried out across a range of temperatures. The temperature at which the oxidation of the present invention is carried out is an important variable affecting aldehyde selectivity. The preferred reaction temperature is in the range from −15° C. to 30° C., most preferably in the range from 0° C. to 10° C. The process of the invention can be carried out in any conventional batch, semi-batch or continuous flow reactor capable of bringing the two immiscible phases is sufficient contact and at the same time capable of maintaining the reaction temperature within the desired range.

In accordance with one embodiment of the present invention, the oxidation is carried out as follows:
1. Preparing an aqueous solution of $NaHCO_3$ and $Na_2B_4O_7$
2. Adding a solution of MeO-TEMPO in an alcohol substrate of Formula I
3. Bringing the pH of the biphasic system into the range 8.6–9.5 using a dilute solution of HCl or $CH_3COOH$
4. Cooling the stirred suspension to about 0–5° C.
5. Starting the metered addition of concentrated bleach solution maintaining the reaction temperature at the desired setting to oxidize the compound of Formula I and
6. Post-addition stirring of the reaction to full conversion of the substrate.

In accordance with another embodiment of the present invention the oxidation is carried out in the presence of a reaction solvent:
1. Preparing an aqueous solution of $NaHCO_3$ and $Na_2B_4O_7$
2. Adding a solution of MeO-TEMPO and alcohol substrate of Formula I in appropriate reaction solvent
3. Bringing the pH of the biphasic system into the range 8.6–9.5 using a dilute solution of HCl or $CH_3COOH$
4. Cooling the stirred suspension to about 0–5° C.
5. Starting the metered addition of concentrated bleach solution maintaining the reaction temperature at the desired setting to oxidize the compound of Formula I and
6. Post-addition stirring of the reaction to full conversion of the substrate.

In accordance with another embodiment of the present invention the oxidation is carried out in presence of a ZrO (acetate)$_2$ co-catalyst and comprises the following steps:
1. Preparing an aqueous solution of $NaHCO_3$ and ZrO (acetate)$_2$ 2. Adding a solution of MeO-TEMPO and alcohol substrate of Formula I
3. Bringing the pH of the biphasic system into the range 8.6–9.5 using a dilute solution of HCl or CH₃COOH
4. Cooling the stirred suspension to about 0–5° C.
5. Starting the metered addition of concentrated bleach solution maintaining the reaction temperature at the desired setting to oxidize the compound of Formula I and
6. Post-addition stirring of the reaction to full conversion of the substrate In another embodiment of the present invention the oxidation is carried out with pre-activated bleach solution and could be described as:
1. Preparing an aqueous solution of NaHCO₃ and Na₂B₄O₇
2. Adding a solution of MeO-TEMPO and alcohol substrate of Formula I in an appropriate reaction solvent
3. Bringing the pH of the biphasic system into the range 8.6–9.5 using a dilute solution of HCl or CH₃COOH
4. Cooling the stirred suspension to about 0–5° C.
5. Starting the metered addition of concentrated bleach solution, the pH of which has been reduced by using dilute solution of HCl or CH₃COOH and
6. Post-addition stirring of the reaction to full conversion of the substrate In the processes of the present invention, the solvent, if used, is preferably selected from the group of aprotic inert solvents such as methylene chloride, chloroform, ethyl acetate, butyl acetate, acetonitrile, tetrahydrofuran, toluene, acetone, diethyl ether, methyl tert-butyl ether, pentane, hexane, heptane and the mixture of the said solvents. Especially preferred solvents are heptane, toluene and ethyl acetate or a mixture of said solvents.

In the inventive processes, the MeO-TEMPO catalyst preferably is used in a concentration of 0.001–10.0% mol, more preferably about 0.1–1% mol. The co-catalyst preferably is used in a concentration of 0.002–20.0% mol, more preferably about 0.2–2 mole percent. If the bleach solution comprises sodium hypochlorite, the sodium hypochlorite preferably is used in about 0.8–1.5 equivalents, more preferably about 1–1.2 equivalents, relative to the alcohol substrate.

Once the reaction is completed, the crude 3,3-dimethylbutyraldehyde is isolated by phase split or by extraction with organic solvent. The solvent used in extraction can be selected from the group of aprotic inert solvents such as methylene chloride, chloroform, ethyl acetate, butyl acetate, methyl acetate, toluene, diethyl ether, methyl tert-butyl ether, pentane, hexane, heptane. Excess solvent may be recycled after isolation of the desired aldehyde. Especially preferred solvents are toluene and ethyl acetate. The crude 3,3-dimethylbutyraldehyde can be recovered in several ways, including distillation, fractional distillation, either batch or continuous, or use of a thin-film evaporator to concentrate the 3,3-dimethylbutyraldehyde. The crude 3,3-dimethylbutyraldehyde can be purified as described in U.S. Pat. No. 5,905,175 or by distillation, fractional distillation, either batch or continuous, or use of a thin-film evaporator. A preferred purification step involves distillation at 100–106° C. and atmospheric pressure to obtain purified 3,3-dimethylbutyraldehyde.

The following examples are given to illustrate the scope of the present invention. The examples are given for illustrative purposes only; the invention embodied herein should not be limited thereto.

EXAMPLE I

Comparative Example

Example I represent a reference oxidation reaction under the conditions analogous to the one (reported in J.Organic Chemistry, 1987, 52, 2559 and J. Organic Chemistry, 1989, 54, 2970), also known as Anelli protocol.

820 mg of 3,3-Dimethyl-1-butanol (8 mmol) and 14.9 mg MeO-TEMPO (0.08 mmol) are dissolved in toluene (20 cc) in a jacketed glass reaction flask, equipped with a thermocouple, an addition port, a Teflon coated magnetic stir bar and a pH probe. Potassium bromide (45.25 mg, 0.4 mmol) and 1310 mg of NaHCO₃ are dissolved in water (21.6 cc) and the aqueous phase is added to the stirred organic fraction at 1000 RPM in the reaction flask. The stirred suspension is cooled to 0° C. and 5.4 g of 12.3% aqueous NaOCl (8.92 mmol) are added via a gas-tight syringe over 5 minutes. The reaction mixture is aged for an additional 30 min and the organic layer sampled for GC assay. The yield of 3,3-dimethylbutyraldehyde is 77% at 30 min and 91% at 60 min reaction time.

The following are the calculated amounts of MeO-TEMPO catalyst, co-catalyst and buffering reagents needed for the manufacture of 1 Kg 3,3-dimethylbutyraldehyde.

TABLE 1

| 1<br>Component | 2<br>8 mmol scale<br>G (cc) | 3<br>1 kg scale<br>Kg (L) |
|---|---|---|
| 3,3-dimethyl-1-butanol | 0.817 | 1.00 |
| Toluene | (20) | (24.5) |
| MeO-TEMPO | 0.0149 | 0.018 |
| H₂O | (22) | (26.9) |
| KBr | 0.0475 | 0.300 |
| NaHCO₃ | 1.31 | 0.160 |
| NaOCl | 5.1 | 6.24 |

The data from Table 1 show the serious deficiencies of the known procedure for TEMPO based bleach oxidation of alcohols, which makes it economically not feasible for practical applications. These include the recommended use of large amounts of chlorinated or other solvents, large amounts of MeO-TEMPO catalyst per unit amount substrate, excessive volumes of aqueous buffer solution and the use of potassium bromide co-catalyst in concentration of at least 5% by weight of the alcohol substrate.

EXAMPLE II

Comparative Example

Example II represents a scaled up synthesis performed in the presence of KBr co-catalyst and NaHCO₃ buffer in the absence of a reaction solvent. Number of improvements are made to allow the use of neat alcohol, such as reduced amount of buffer, sharply reduced amount of KBr, slow addition of the bleach solution and continuous maintenance of the pH in the stage of the bleach addition and further during the post addition reaction. Example II is the closest approximation to the Anelli conditions and although it is a qualitatively new level on its own compared to the prior art, is considered here for reference purposes only.

16.9 g of 3,3-Dimethyl-1-butanol (117.3 mmol) and 0.0765 g MeO-TEMPO (0.411 mmol) are charged in a jacketed glass reaction flask, equipped with a thermocouple, an addition port, a Teflon coated magnetic stir bar and a pH probe. Potassium bromide (0.011 g, 0.104 mmol) and 0.676 g. NaHCO₃ are dissolved in water (12.4 cc) and the aqueous solution is added to the stirred organic fraction at 1000 RPM in the reaction flask. The stirred suspension is cooled to 0° C. and the emulsion is re-adjusted to pH=8.4 using 50% solution of HCl. When the temperature of the reactants reached 0° C., 82 g (133 mmol) of 12.1% aqueous NaOCl solution are pumped in via a gas-tight syringe over 90 minutes. During the bleach addition, the pH is maintained at 8.3–8.4 levels using few drops of 50% aqueous HCl. The reaction mixture is stirred for an additional 120 min at 0° C. and the organic layer is sampled for GC assay. The reaction in this second stage is kept at pH 8.4 by addition of 0.2–0.25 cc aqueous solution of NaOH (50% concentration). The yield of 3,3-dimethylbutyraldehyde is 89.7% at 60 min and 91.5% at 90 min reaction time.

EXAMPLE III

Example III represents an oxidation in which the $Na_2B_4O_7$ is used as co-catalyst and the $NaHCO_3$ is the buffering agent. The example is needed to show that the $Na_2B_4O_7$ co-catalyst is more efficient then the known KBr based system (compare the results with those from Example II).

16.9 g of 3,3-Dimethyl-1-butanol (117.3 mmol) and 0.0765 g MeO-TEMPO (0.411 mmol) are charged in a jacketed glass reaction flask as in Example I. Sodium borate (0.380 g, 1.0 mmol) and 0.676 g $NaHCO_3$ are dissolved in water (17 cc) and the aqueous solution is added to the stirred organic fraction at 1000 RPM in the reaction flask. The stirred suspension is cooled to 0° C. and the emulsion is re-adjusted to pH=8.4 using 50% solution of $CH_3COOH$. When the temperature of the reactants reached 0° C., 77.5 g (126 mmol) of 12.1% aqueous NaOCl solution are pumped in via a gas-tight syringe over 90 minutes (The pH of the bleach solution was adjusted to 10 using 50% aqueous $CH_3COOH$). During the bleach addition, the pH was maintained at 8.3–8.4 levels using few drops of 50% aqueous $CH_3COOH$. The reaction mixture is stirred for an additional 120 min at 0° C. and the organic layer is sampled for GC assay. The reaction in this second stage was kept at pH 8.4 by addition of 0.2–0.25 cc aqueous solution of NaOH (50% concentration). The yield of 3,3-dimethylbutyraldehyde is 94.0% at 60 min and 96.0% at 90 min reaction time.

EXAMPLE IV

Example IV represents an oxidation in which the KBr co-catalyst and the $NaHCO_3$ buffer were removed and replaced with $Na_2B_4O_7$ additive.

16.9 g of 3,3-Dimethyl-1-butanol (117.3 mmol) and 0.0765 g MeO-TEMPO (0.411 mmol) are charged in a jacketed glass reaction flask as in Example I. Sodium borate (0.380 g, 1.0 mmol) is dissolved in water (12.0 cc) and the aqueous solution is added to the stirred organic fraction at 1000 RPM in the reaction flask. The stirred suspension is cooled to 0° C. and the emulsion is re-adjusted to pH=8.4 using 50% solution of $CH_3COOH$. When the temperature of the reactants reached 0° C., 75.5 g (122 mmol) of 12.1% aqueous NaOCl solution are pumped in via a gas-tight syringe over 90 minutes. During the bleach addition, the pH was maintained at 8.3–8.4 levels using a few drops of 50% aqueous $CH_3COOH$. The reaction mixture is stirred for an additional 120 min at 0° C. and the organic layer is sampled for GC assay. The reaction in this second stage was kept at pH 8.4 by addition of 0.2–0.25 cc aqueous solution of NaOH (50% concentration). The yield of 3,3-dimethylbutyraldehyde is 90.0% at 60 min and 91.0% at 90 min reaction time.

EXAMPLE V

Example V represents an oxidation in which the KBr co-catalyst and the $NaHCO_3$ buffer were removed and they were replaced with $Na_2B_4O_7$—$Zr(acetate)_2$ additive.

16.9 g of 3,3-Dimethyl-1-butanol (117.3 mmol) and 0.0765 g MeO TEMPO (0.411 mmol) are charged in a jacketed glass reaction flask as in Example I. Sodium borate (0.380 g, 1.0 mmol) and $Zr(acetate)_2$ (0.2 g solution, 0.1 mmol) are dissolved in water (12.0 cc) and the aqueous solution is added to the stirred organic fraction at 1000 RPM in the reaction flask. The stirred suspension is cooled to 0° C. and the emulsion is re-adjusted to pH=8.4 using 50% solution of $CH_3COOH$. When the temperature of the reactants reached 0° C., 75.5 g (122 mmol) of 12.1% aqueous NaOCl solution are pumped in via a gas-tight syringe over 90 minutes (The pH of the bleach solution was adjusted to 10 using 50% aqueous $CH_3COOH$). During the bleach addition the pH was maintained at 8.3–8.4 levels using few drops of 50% aqueous $CH_3COOH$. The reaction mixture is stirred for an additional 120 min at 0° C. and the organic layer is sampled for GC assay. The reaction in this second stage was kept at pH 8.4 by addition of 0.2–0.25 cc aqueous solution of NaOH (50% concentration). The yield of 3,3-dimethylbutyraldehyde is 95.0% at 60 min and 93.0% at 90 min reaction time.

EXAMPLE VI

Example VI represents an oxidation in which the KBr co-catalyst and the $Na_2B_4O_7$ are simultaneously present.

16.9 g of 3,3-Dimethyl-1-butanol (117.3 mmol) and 0.0765 g MeO-TEMPO (0.411 mmol) are charged in a jacketed glass reaction flask as in Example I. Sodium borate (0.380 g, 1.0 mmol) and potassium bromide (0.011 g, 0.104 mmol) are dissolved in water (12.0 cc) and the aqueous solution is added to the stirred organic fraction at 1000 RPM in the reaction flask. The stirred suspension is cooled to 0° C. and the emulsion is re-adjusted to pH 8.4 using 50% solution of $CH_3COOH$. When the temperature of the reactants reached 0° C., 75.5 g (122 mmol) of 12.1% aqueous NaOCl solution are pumped in via a gas-tight syringe over 90 minutes (The pH of the bleach solution was adjusted to 10 using 50% aqueous $CH_3COOH$). During the bleach addition the pH was maintained at 8.3–8.4 levels using a few drops of 50% aqueous $CH_3COOH$. The reaction mixture is stirred for an additional 120 min at 0° C. and the organic layer is sampled for GC assay. The reaction in this second stage was kept at pH 8.4 by addition of 0.2–0.25 cc aqueous solution of NaOH (50% concentration). The yield of 3,3-dimethylbutyraldehyde is 94.0% at 60 min and 95.0% at 90 min reaction time. This yield is equivalent to the yield of Example III in which no potassium bromide was used.

EXAMPLE VII

Example VII is similar to VI but it exemplifies the robustness of the new catalytic system. Instead of continuously monitoring and maintaining the pH of the emulsion in the second stage, the required amount of NaOH solution was introduced at once at the onset of the second stage of the oxidation. All other concentrations and ratios are the same as in Example III.

16.9 g of 3,3-Dimethyl-1-butanol (117.3 mmol) and 0.0765 g MeO-TEMPO (0.411 mmol) are charged in a jacketed glass reaction flask as in Example I. Sodium borate (0.380 g, 1.0 mmol) and 0.676 g $NaHCO_3$ are dissolved in water (17 cc) and the aqueous solution is added to the stirred organic fraction at 1000 RPM in the reaction flask. The stirred suspension is cooled to 0° C. and the emulsion is re-adjusted to pH 8.4 using 50% solution of $CH_3COOH$. When the temperature of the reactants reached 0° C., 77.5 g (126 mmol) of 12.1% aqueous NaOCl solution are pumped in via a gas-tight syringe over 90 minutes (The pH of the bleach solution was adjusted to 10 using 50% aqueous $CH_3COOH$). During the bleach addition, the pH was maintained at 8.3–8.4 levels using few drops of 50% aqueous $CH_3COOH$. The reaction mixture is stirred for an additional 120 min at 0° C. and the organic layer is sampled for GC assay. In this Example, 0.2–0.25 cc aqueous solution of NaOH (50% concentration) was added immediately after the bleach addition was completed and no efforts were made to maintain the pH of the emulsion. The yield of 3,3-dimethylbutyraldehyde is 97.0% at 60 min and 94.0% at 90 min reaction time.

EXAMPLE VIII

Example VIII is similar to VII but the amount of MeO-TEMPO is reduced twice. All other concentrations and ratios are the same as in Example VII.

16.9 g of 3,3-Dimethyl-1-butanol (117.3 mmol) and 0.0382 g MeO-TEMPO (0.205 mmol) are charged in a jacketed glass reaction flask as in Example I. Sodium borate (0.380 g, 1.0 mmol) and 0.676 g $NaHCO_3$ are dissolved in water (17 cc) and the aqueous solution is added to the stirred organic fraction at 1000 RPM in the reaction flask. The stirred suspension is cooled to 0° C. and the emulsion is re-adjusted to pH=8.4 using 50% solution of $CH_3COOH$. When the temperature of the reactants reached 0° C., 77.5 g (126 mmol) of 12.1% aqueous NaOCl solution are pumped in via a gas-tight syringe over 90 minutes (The pH of the bleach solution was adjusted to 10 using 50% aqueous $CH_3COOH$). During the bleach addition the pH was maintained at 8.3–8.4 levels using few drops of 50% aqueous $CH_3COOH$. The reaction mixture is stirred for an additional 120 min at 0° C. and the organic layer is sampled for GC assay. In this Example, 0.2–0.25 cc aqueous solution of NaOH (50% concentration) was added immediately after the bleach addition was completed and no efforts were made to maintain the pH of the emulsion. The yield of 3,3-dimethylbutyraldehyde is 94.0% at 60 min and 99.0% at 90 min reaction time.

EXAMPLE IX

Example IX sheds light on the role that the $Na_2B_4O_7$ plays as an independent co-catalyst to the TEMPO system. In this Example, the sodium borate was completely removed and it was replaced with additional, equimolar amount $NaHCO_3$. The complete deterioration of the aldehyde yield shows that the presence of $Na_2B_4O_7$ is crucial in achieving catalyst efficiency under the standard reaction conditions (compare with example VIII).

16.9 g of 3,3-Dimethyl-1-butanol (117.3 mmol) and 0.0382 g MeO-TEMPO (0.205 mmol) are charged in a jacketed glass reaction flask as in Example I. $NaHCO_3$ 0.757 g $NaHCO_3$ are dissolved in water (17 cc) and the aqueous solution is added to the stirred at 1000 RPM organic fraction in the reaction flask. The stirred suspension is cooled to 0° C. and the emulsion is re-adjusted to pH 8.4 using 50% solution of $CH_3COOH$. When the temperature of the reactants reached 0° C., 77.5 g (126 mmol) of 12.1% aqueous NaOCl solution are pumped in via a gas-tight syringe over 90 minutes (The pH of the bleach solution was adjusted to 10 using 50% aqueous $CH_3COOH$). During the bleach addition, the pH was maintained at 8.3–8.4 levels using a few drops of 50% aqueous $CH_3COOH$. The reaction mixture is stirred for an additional 120 min at 0° C. and the organic layer is sampled for GC assay. In this Example, 0.2–0.25 cc aqueous solution of NaOH (50% concentration) was added immediately after the bleach addition was completed and no efforts were made to maintain the pH of the emulsion. The yield of 3,3-dimethylbutyraldehyde is 67.0% at 60 min and 67.0% at 90 min reaction time.

The next series of examples show the use of different 4-substituted TEMPO catalysts and $Na_2B_4O_7$ co-catalyst.

EXAMPLE X 12.2 g of 3,3-Dimethyl-1-butanol of 98% purity (117.3 mmol) and 0.043 g MeO-TEMPO (0.223 mmol) are charged in a jacketed glass reaction flask as in Example I. Sodium borate (0.294 g, 0.76 mmol), $NaHCO_3$ (1.472 g, 17.5 mmol) and NaCl (2 g) are dissolved in water (25 cc) and the aqueous solution is added to the stirred organic fraction at 1000 RPM in the reaction flask. The stirred suspension is cooled to 0° C. and the emulsion is re-adjusted to pH 8.6 using 40% solution of NaOH. When the temperature of the reactants reached 0° C., 69.8 g (123.1 mmol) of 13.1% aqueous NaOCl solution are pumped in via a gas-tight syringe over 55 minutes. The reaction mixture is stirred for an additional 15 min at 0° C. and the organic layer is sampled for GC assay. The yield of 3,3-dimethylbutyraldehyde is 90.6% at 2 min of post bleach-addition time and 92.1% at 15 min reaction time.

EXAMPLE XI 12.2 g of 3,3-Dimethyl-1-butanol of 98% purity (117.3 mmol) and 0.036 g TEMPO (0.223 mmol) are charged in a jacketed glass reaction flask as in Example I. Sodium borate (0.294 g, 0.76 mmol), $NaHCO_3$ (1.472 g, 17.5 mmol) and NaCl (2 g) are dissolved in water (25 cc) and the aqueous solution is added to the stirred organic fraction at 1000 RPM in the reaction flask. The stirred suspension is cooled to 0° C. and the emulsion is re-adjusted to pH 8.6 using 40% solution of NaOH. When the temperature of the reactants reached 0° C., 69.8 g (123.1 mmol) of 13.1% aqueous NaOCl solution are pumped in via a gas-tight syringe over 55 minutes. The reaction mixture is stirred for an additional 15 min at 0° C. and the organic layer is sampled for GC assay. The yield of 3,3-dimethylbutyraldehyde is 87.4% at 2 min of post bleach-addition time and 91.2% at 15 min reaction time.

EXAMPLE XII 12.2 g of 3,3-Dimethyl-1-butanol of 98% purity (117.3 mmol) and 0.049 g 4-Acetamido-TEMPO (0.223 mmol) are charged in a jacketed glass reaction flask as in Example I. Sodium borate (0.294 g, 0.76 mmol), $NaHCO_3$ (1.472 g, 17.5 mmol) and NaCl (2 g) are dissolved in water (25 cc) and the aqueous solution is added to the stirred organic fraction at 1000 RPM in the reaction flask. The stirred suspension is cooled to 0° C. and the emulsion is re-adjusted to pH 8.6 using 40% solution of NaOH. When the temperature of the reactants reached 0° C., 69.8 g (123.1 mmol) of 13.1% aqueous NaOCl solution are pumped in via a gas-tight syringe over 55 minutes. The reaction mixture is stirred for an additional 15 min at 0° C. and the organic layer is sampled for GC assay. The yield of 3,3-dimethylbutyraldehyde is 88.3% at 2 min of post bleach-addition time and 92.1% at 15 min reaction time.

EXAMPLE XIII 8.6 g of heptan-1-ol of 98% purity (72.8 mmol), toluene (10 cc) and 0.047 g MeO-TEMPO (0.252 mmol) are charged in a jacketed glass reaction flask as in Example I. Sodium borate (0.129 g, 0.338 mmol), NaHCO$_3$ (0.43 g) are dissolved in water (15 cc) and the aqueous solution is added to the stirred organic fraction at 1000 RPM in the reaction flask. The stirred suspension is cooled to 0° C. and the emulsion is re-adjusted to pH=8.6 using 50% solution of CH$_3$COOH. When the temperature of the reactants reached 0° C., 47.7 g (84.0 mmol) of 13.1% aqueous NaOCl solution are pumped in via a gas-tight syringe over 20 minutes. The reaction mixture is stirred for an additional 15 min at 0° C. and the organic layer is sampled for GC assay. The yield of heptanal is 93.0% at 2 min of post bleach-addition time.

EXAMPLE XIV 7.5 g of hexan-1-ol of 98% purity (72.8 mmol), toluene (10 cc) and 0.047 g MeO-TEMPO (0.252 mmol) are charged in a jacketed glass reaction flask as in Example I. Sodium borate (0.129 g, 0.338 mmol), NaHCO$_3$ (0.43 g) are dissolved in water (15 cc) and the aqueous solution is added to the stirred organic fraction at 1000 RPM in the reaction flask. The stirred suspension is cooled to 0° C. and the emulsion is re-adjusted to pH 8.6 using 50% solution of CH$_3$COOH. When the temperature of the reactants reached 0° C., 47.7 g (84.0 mmol) of 13.1% aqueous NaOCl solution are pumped in via a gas-tight syringe over 20 minutes. The reaction mixture is stirred for an additional 15 min at 0° C. and the organic layer is sampled for GC assay. The yield of hexanal is 90.0% at 2 min of post bleach-addition time.

EXAMPLE XV 7.9 g of benzyl alcohol 99% purity (72.3 mmol), toluene (10 cc) and 0.047 g MeO-TEMPO (0.252 mmol) are charged in a jacketed glass reaction flask as in Example I. Sodium borate (0.129 g, 0.338 mmol), NaHCO$_3$ (0.43 g) are dissolved in water (15 cc) and the aqueous solution is added to the stirred organic fraction at 1000 RPM in the reaction flask. The stirred suspension is cooled to 0° C. and the emulsion is re-adjusted to pH 8.6 using 50% solution of CH$_3$COOH. When the temperature of the reactants reached 0° C., 47.7 g (84.0 mmol) of 13.1% aqueous NaOCl solution are pumped in via a gas-tight syringe over 20 minutes. The reaction mixture is stirred for an additional 15 min at 0° C. and the organic layer is sampled for GC assay. The yield of benzaldehyde is 100.0% at 2 min of post bleach-addition time.

EXAMPLE XVI 8.36 g of 4-methylcyclohexanol of 98% purity (71.7 mmol), toluene (10 cc) and 0.047 g MeO-TEMPO (0.252 mmol) are charged in a jacketed glass reaction flask as in Example I. Sodium borate (0.129 g, 0.338 mmol), NaHCO$_3$ (0.43 g) are dissolved in water (15 cc) and the aqueous solution is added to the stirred organic fraction at 1000 RPM in the reaction flask. The stirred suspension is cooled to 0° C. and the emulsion is re-adjusted to pH 8.4 using 50% solution of CH$_3$COOH. When the temperature of the reactants reached 0° C., 47.7 g (84.0 mmol) of 13.1% aqueous NaOCl solution are pumped in via a gas-tight syringe over 20 minutes. The reaction mixture is stirred for an additional 5 min at 0° C. and the organic layer is sampled for GC assay. The yield of 4-methylcyclohexanone is 94.0% at 5 min of post bleach-addition time.

EXAMPLE XVII 7.55 g of 4-methy-2-pentanol of 99% purity (73.2 mmol), toluene (10 cc) and 0.047 g MeO-TEMPO (0.252 mmol) are charged in a jacketed glass reaction flask as in Example I. Sodium borate (0.129 g, 0.338 mmol), NaHCO$_3$ (0.43 g) are dissolved in water (15 cc) and the aqueous solution is added to the stirred organic fraction at 1000 RPM in the reaction flask. The stirred suspension is cooled to 0° C. and the emulsion is re-adjusted to pH 8.4 using 50% solution of CH$_3$COOH. When the temperature of the reactants reached 0° C., 47.7 g (84.0 mmol) of 13.1% aqueous NaOCl solution are pumped in via a gas-tight syringe over 20 minutes. The reaction mixture is stirred for an additional 5 min at 0° C. and the organic layer is sampled for GC assay. The yield of 4-methyl-2-pentanone is 77.0% at 5 min of post bleach-addition time. The same reaction run at 22° C. produced the desired 4-methyl-2-pentanon at 92% yield.

EXAMPLE XVIII 8.68 g of heptanol-1 of 98% purity (73.2 mmol), toluene (10 cc) and 0.047 g MeO-TEMPO (0.252 mmol) are charged in a jacketed glass reaction flask as in Example I. Sodium borate (0.129 g, 0.338 mmol), NaHCO$_3$ (0.43 g) are dissolved in water (15 cc) and the aqueous solution is added to the stirred organic fraction at 1000 RPM in the reaction flask. The stirred suspension is cooled to 0° C. and the emulsion is re-adjusted to pH 8.4 using 50% solution of CH$_3$COOH. When the temperature of the reactants reached 0° C., 95.4 g (168.0 mmol) of 13.1% aqueous NaOCl solution are pumped in via a gas-tight syringe over 40 minutes. The reaction mixture is stirred for an additional 5 min at 0° C. and the organic layer is sampled for GC assay. The yield of heptanoic acid is 83.0% at 5 min of post bleach-addition time.

What is claimed is:

1. A process for oxidizing primary and secondary alcohols to aldehydes and ketones, said process comprising reacting the primary or secondary alcohol with an oxidant wherein said alcohol is in a solution including a catalyst selected from the group comprising 2,2,6,6,-tetramethylpiperidinyloxy catalysts and further in the presence of a co-catalyst, wherein the co-catalyst is selected from the group comprising oxymetal ions and salts thereof, said alcohol acting as the substrate in said solution.

2. The process of claim 1, where said primary and secondary alcohols are selected from the group comprising methanol, ethanol, n- and isopropyl alcohol, n-, iso- and sec-butyl alcohol, pentyl alcohol, hexyl alcohol, neopentyl alcohol, neohexyl alcohol, octyl alcohol, lauryl alcohol, tridecyl alcohol, myristyl alcohol, nonadecyl alcohol, eicosyl alcohol, unsaturated alcohols including but not limited to allyl alcohol, crotyl alcohol and propargyl alcohol, and aromatic alcohols including but not limited to benzyl alcohol, phenyl ethanol, and phenyl propanol.

3. The process of claim 1, wherein said 2,2,6,6,-tetramethylpiperidinyloxy catalyst is selected from the group consisting of catalysts having the formulas:

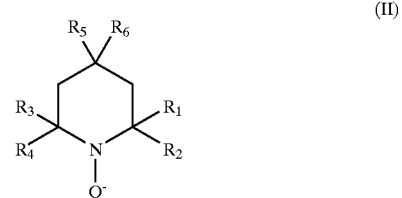

(II)

-continued

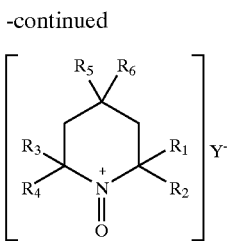

(III)

wherein $R_1$, $R_2$, $R_3$ and $R_4$ independently lower alkyl or substituted alkyl groups of the same or different structures, $R_5$ and $R_6$ are both hydrogen or are lower alkoxy or one is hydrogen and the other is lower alkoxy, hydroxy, amino, alkyl or dialkylamino, alkylcarbonyloxy, alkylcarbonylamino, or can be jointly substituted by an oxygen or a ketal, and the $Y^-$ is an anion.

4. The process of claim 3 wherein the 2,2,6,6,-tetramethylpiperidinyloxy catalyst is present in an amount of 0.001–10 mol % of the substrate alcohol.

5. The process of claim 3 wherein said TEMPO based catalyst is selected from the group consisting of 4-methoxy-TEMPO, 4-ethoxy-TEMPO, 4-acetoxy-TEMPO, 4-acetamino-TEMPO, 4-hydroxy-TEMPO, 4-benzoyloxy-TEMPO, 4-amino—TEMPO, N, N-dimethylamino-TEMPO, 4-oxo-TEMPO, poly [(6-[1,1,3,3-tetramethylbutyl)amino]-s-triazine-2,4-diyl], [(2,2,6,6-tetramethyl-4-piperidyl)imino] hexamethylene[(2,2,6,6-tetramethyl-4-piperidinyl)imino]] and combination of these.

6. The process of claim 1 wherein the co-catalyst is selected from the group of oxymetal cations comprising $TiO^{2+}$, $VO^{2+}$, $CrO_2^{2+}$, $ZrO^{2+}$, $MoO_2^{2+}$, $WO_2^{2+}$ and the group of anions comprising $MoO_4^{2-}$, $WO_4^{2-}$, $VO_3^-$, $H_2PO_4^{2-}$, $B_4O_7^{2-}$.

7. The process of claim 6 wherein the co-catalyst is $Na_2B_4O_7$ or ZrO (acetate)$_2$.

8. The process of claim 6, wherein the co-catalyst concentration is 0.01–20% mol of the substrate alcohol.

9. The process of claim 1, wherein the oxidant is selected from the group comprising sodium hypochlorite, potassium hypochlorite, calcium hypochlorite, sodium chlorite, hydrogen peroxide, tert-butyl hydroperoxide, trichloroisocyanuric acid, peracetic acid, performic acid, trichloroperacetic acid and trifluoroperacetic acid.

10. The process of claim 9 wherein the ratio between the oxidant and the alcohol is in the range of from about 1:0.8 to 1:1.5.

11. The process of claim 1, further comprising the addition of one or more additional solvents to the alcohol solution.

12. The process of claim 11 wherein said solvent is selected from the group comprising: water, acetonitrile, acetone, tetrahydrofuran, benzene, toluene, methyl tert-butyl ether, methylene chloride, chloroform, carbon tetrachloride, pentane, hexane, heptane, ethyl acetate, methyl acetate and a mixture of solvents from the group above.

13. The process of claim 1, wherein the oxidation is carried out in absence of an additional solvent.

14. The process of claim 1, wherein a buffer solution is added to the alcohol solution.

15. The process of claim 14 wherein said buffer solution comprises a solution of $NaHCO_3$, $KHCO_3$, $Na_2CO_3$, $K_2CO_3$, $K_2PO_4$, $Na_2HPO_4$, $NaH_2PO_4$, $K_2HPO_4$, $KH_2PO_4$, NaOAc and any combination thereof sufficient to maintain a pH of from about 4 to about 12.

16. The process of claim 1, wherein the reaction temperature is maintained in the range of $-10°$ C. to $50°$ C.

17. The process of claim 14, wherein a bleach solution is added to the solution of alcohol and aqueous buffer while maintaining the pH of the emulsion in the range of about pH 4–12.

18. The process of claim 17, wherein the addition time for the bleach solution is between complete addition at one time and 10 hours and the post addition reaction is continued for an additional 0 to 10 hours.

19. The process of claim 18, wherein a solution of the catalyst in the alcohol substrate is added over the buffered bleach solution, containing the co-catalyst over extended period of time while maintaining the pH of the emulsion in the range of about pH 4–12.

20. The process of claim 1 wherein the addition time for the catalyst-alcohol solution is between complete addition at one time and 10 hours and the post addition reaction is continued for an additional 0 to 30 hours.

21. The method of claim 1 comprising the additional step of purification of the crude aldehyde or ketone via distillation, fractional distillation, either batch or continuous or a thin-film evaporator.

22. A process for the production of 3,3-dimethylbutyraldehyde, comprising the step of reacting 3,3-dimethylbutanol with an oxidant wherein said 3,3-dimethylbutanol is in a solution including a catalyst selected from the group comprising 2,2,6,6,-tetramethylpiperidinyloxy catalysts and further in the presence of a co-catalyst selected from the group comprising the group of oxymetal cations comprising $TiO^{2+}$, $VO^{2+}$, $CrO_2^{2+}$, $ZrO^{2+}$, $MoO_2^{2+}$, $WO_2^{2+}$ and the group of anions comprising $MoO_4^{2-}$, $WO_4^{2-}$, $VO_3^-$, $H_2PO_4^{2-}$, $B_4O_7^{2-}$.

23. The process of claim 22 wherein said oxidant is selected from the group comprising comprising sodium hypochlorite, potassium hypochlorite, calcium hypochlorite, sodium chlorite, hydrogen peroxide, tert-butyl hydroperoxide, trichloroisocyanuric acid, peracetic acid, performic acid, trichloroperacetic acid and trifluoroperacetic acid.

24. The process of claim 22 wherein the ratio between the oxidant and the alcohol is in the range of from about 1:0.8 to 1:1.5.

25. The process of claim 22 further comprising the addition of an additional solvent to the alcohol solution.

26. The process of claim 25 wherein said solvent is selected from the group comprising: water, acetonitrile, acetone, tetrahydrofuran, benzene, toluene, methyl tert-butyl ether, methylene chloride, chloroform, carbon tetrachloride, pentane, hexane, heptane, ethyl acetate, methyl acetate and a mixture of solvents from the group above.

27. The process of claim 22 wherein said process is carried out in the absence of a solvent.

28. The process of claim 22 wherein a buffer solution is added to the alcohol solution.

29. The process of claim 28 wherein said buffer solution comprises a solution of $NaHCO_3$, $KHCO_3$, $Na_2CO_3$, $K_2CO_3$, $K_2PO_4$, $Na_2HPO_4$, $NaH_2PO_4$, $K_2HPO_4$, $KH_2PO_4$, NaOAc and any combination thereof sufficient to maintain a pH of from about 4 to about 12.

30. The process of claim 29 wherein a bleach solution is added to the solution of alcohol and aqueous buffer while maintaining the pH of the emulsion in the range of about pH 4–12.

31. The process of claim 29 wherein the addition time for the bleach solution is between complete addition at one time and 10 hours and the post addition reaction time is continued for an additional 0 to 10 hours.

32. A process for oxidizing primary and secondary alcohols to aldehydes and ketones, said process comprising reacting the primary or secondary alcohol with an oxidant wherein said alcohol is in a solution including a two or more catalysts each selected from the group comprising 2,2,6,6,-tetramethylpiperidinyloxy catalysts and further in the presence of a co-catalyst, wherein the co-catalyst is selected from the group comprising oxymetal ions and salts thereof, said alcohol acting as the substrate in said solution.

* * * * *